US011247014B2

(12) United States Patent
Koizumi et al.

(10) Patent No.: US 11,247,014 B2
(45) Date of Patent: Feb. 15, 2022

(54) OXYGEN CONCENTRATOR

(71) Applicant: Teijin Pharma Limited, Tokyo (JP)

(72) Inventors: Ryo Koizumi, Tokyo (JP); Yuki Yamaura, Tokyo (JP)

(73) Assignee: Teijin Pharma Limited, Tokyo (JP)

( * ) Notice: Subject to any disclaimer, the term of this patent is extended or adjusted under 35 U.S.C. 154(b) by 795 days.

(21) Appl. No.: 16/076,187

(22) PCT Filed: Feb. 22, 2017

(86) PCT No.: PCT/JP2017/008044
§ 371 (c)(1),
(2) Date: Aug. 7, 2018

(87) PCT Pub. No.: WO2017/146271
PCT Pub. Date: Aug. 31, 2017

(65) Prior Publication Data
US 2021/0178103 A1 Jun. 17, 2021

(30) Foreign Application Priority Data
Feb. 24, 2016 (JP) .............................. JP2016-033158

(51) Int. Cl.
*B01D 53/047* (2006.01)
*A61M 16/00* (2006.01)
(Continued)

(52) U.S. Cl.
CPC ...... *A61M 16/101* (2014.02); *A61M 16/0063* (2014.02); *B01D 53/047* (2013.01);
(Continued)

(58) Field of Classification Search
CPC ............ A61M 16/101; A61M 16/0063; A61M 2202/0266; A61M 2206/3368;
(Continued)

(56) References Cited

U.S. PATENT DOCUMENTS

| 7,445,663 B1 | 11/2008 | Hunter et al. |
| 2008/0110338 A1 | 5/2008 | Taylor et al. |

(Continued)

FOREIGN PATENT DOCUMENTS

| CN | 104640592 A | 5/2015 |
| CN | 104755123 A | 7/2015 |

(Continued)

OTHER PUBLICATIONS

Machine generated English translation of JP 2014-057693, puglixhed Apr. 2014.*
Office Action, dated May 18, 2020, issued by The State Intellectual Property Office of People's Republic English of China in Chinese Patent Application No. 201780013510.4.
Communication, dated Feb. 21, 2019, issued by the European Patent Office in European Application No. 17 75 6705.
(Continued)

*Primary Examiner* — Frank M Lawrence, Jr.
(74) *Attorney, Agent, or Firm* — Sughrue Mion, PLLC

(57) ABSTRACT

An oxygen concentrator is provided with a controller for recovering an oxygen concentration to a level suitable for treatment in a short period of time by selecting an optimum purge time corresponding to the deterioration state of an adsorbent. The judgment of moisture-absorption deterioration is performed when the detected value of the oxygen concentration sensor is equal to or less than a control value of the oxygen concentration in the oxygen-enriched gas and the detected value of the pressure sensor is equal to or more than an adsorption pressure at which the oxygen concentration increases significantly before and after the control to reduce the purge time, and control of reducing a time for the purge step shorter than a preset time is performed.

8 Claims, 7 Drawing Sheets

(51) Int. Cl.
*C01B 13/02* (2006.01)
*A61M 16/10* (2006.01)
*B01D 53/04* (2006.01)
*B01D 53/26* (2006.01)
*B01D 53/30* (2006.01)

(52) U.S. Cl.
CPC ..... *B01D 53/0415* (2013.01); *B01D 53/0446* (2013.01); *B01D 53/261* (2013.01); *B01D 53/30* (2013.01); *C01B 13/0259* (2013.01); *A61M 2202/0266* (2013.01); *A61M 2205/3368* (2013.01); *B01D 2253/108* (2013.01); *B01D 2256/12* (2013.01); *B01D 2257/102* (2013.01); *B01D 2257/80* (2013.01); *B01D 2259/402* (2013.01); *B01D 2259/40009* (2013.01); *B01D 2259/40054* (2013.01); *B01D 2259/4533* (2013.01); *C01B 2210/0014* (2013.01); *C01B 2210/0046* (2013.01)

(58) Field of Classification Search
CPC ........ C01B 13/0259; C01B 2210/0014; C01B 2210/0046; B01D 53/04; B01D 53/0415; B01D 53/0446; B01D 53/047; B01D 53/261; B01D 53/30; B01D 2253/108; B01D 2256/12; B01D 2257/102; B01D 2257/80; B01D 2259/40009; B01D 2259/40054; B01D 2259/402; B01D 2259/4533
USPC .......... 95/96, 130, 8, 11, 12, 14, 15, 19, 21; 96/109, 111–113, 121
See application file for complete search history.

(56) References Cited

U.S. PATENT DOCUMENTS

| | | | |
|---|---|---|---|
| 2009/0229460 A1* | 9/2009 | McClain | B01D 53/0446 95/96 |
| 2012/0272966 A1* | 11/2012 | Ando | B01D 53/047 128/205.27 |
| 2014/0137744 A1* | 5/2014 | Wilkinson | B01D 53/047 96/152 |
| 2015/0217078 A1* | 8/2015 | Kobayashi | A61M 16/0063 128/202.26 |

FOREIGN PATENT DOCUMENTS

| | | |
|---|---|---|
| EP | 2898915 A1 | 7/2015 |
| JP | 2000-516854 A | 12/2000 |
| JP | 2002-253675 A | 9/2002 |
| JP | 2008-125885 A | 6/2008 |
| JP | 2013-013497 A | 1/2013 |
| JP | 2013-052021 A | 3/2013 |
| JP | 2014-057693 A | 4/2014 |
| WO | 2011/052803 A1 | 5/2011 |
| WO | 2014/046297 A1 | 3/2014 |

OTHER PUBLICATIONS

Communication, dated Apr. 16, 2019, issued by the Japanese Patent Office in Japanese Application No. 2018-501830 (with English translation).
International Search Report for PCT/JP2017/008044, dated May 30, 2017.

* cited by examiner

OXYGEN CONCENTRATOR

CROSS REFERENCE TO RELATED APPLICATIONS

This Application is a National Stage of International Application No. PCT/JP2017/008044 filed Feb. 22, 2017, claiming priority based on Japanese Patent Application No. 2016-033158 filed Feb. 24, 2016.

TECHNICAL FIELD

The present invention relates to a pressure swing adsorption-type oxygen concentrator using an adsorbent that preferentially adsorbs nitrogen relative to oxygen. Specifically, the present invention relates to a medical oxygen concentrator used for oxygen inhalation therapy that is performed for a patient with chronic respiratory disease and the like. More specifically, the present invention relates to an oxygen concentrator that can be operated while judging a degree of deterioration of the adsorbent from pressure and concentration and switching an operating condition to an optimum one corresponding to the degree of deterioration.

BACKGROUND ART

In recent years, the number of patients suffering from respiratory system diseases such as asthma, pulmonary emphysema, chronic bronchitis and the like has tended to increase. One of the most effective therapeutic methods for these diseases is oxygen inhalation therapy. In such oxygen inhalation therapy, oxygen gas or oxygen-enriched gas is inhaled by patients. An oxygen concentrator, liquid oxygen or oxygen cylinder, and the like are known as an oxygen supply source used for the oxygen inhalation therapy. However, the oxygen concentrator is mainly used for home oxygen therapy because it is convenient to use and easy for maintenance and management.

An oxygen concentrator is a device to supply oxygen to a user by concentrating oxygen that makes up about 21% of the air and as such device, there are a membrane-type oxygen concentrator that uses a membrane which selectively permeate oxygen and a pressure swing adsorption-type oxygen concentrator that uses an adsorbent which can preferentially adsorbs nitrogen or oxygen. A pressure swing adsorption-type oxygen concentrator is mainly used because it can obtain highly concentrated oxygen over 90%.

The pressure swing adsorption-type oxygen concentrator can continuously generate a highly concentrated oxygen gas by repeating alternately: an adsorption step in which, by supplying air compressed by a compressor into an adsorption cylinder packed with molecular sieve zeolite such as 5A type, 13X type, Li-X type, or the like as an adsorbent which adsorbs nitrogen selectively relative to oxygen, nitrogen is adsorbed by the adsorbent to obtain a gas enriched with oxygen which is not adsorbed; a desorption step in which pressure inside the adsorption cylinder is reduced to atmospheric pressure or less to desorb and discharge nitrogen adsorbed by the adsorbent: and a purge step in which regeneration of the adsorbent is accelerated by purging the adsorption cylinder in the desorption step by using a portion of the oxygen-enriched gas generated.

Such a zeolite adsorbent has a property of adsorbing moisture very well, in addition to specific gases such as nitrogen and oxygen and, therefore, has a problem that the adsorbent deteriorates over time due to adsorption of moisture in raw material air and the concentration of oxygen generated gradually decreases. During operation of the oxygen concentrator, a large amount of moisture is discharged together with nitrogen in the desorption step in which nitrogen adsorbed by the adsorbent is desorbed and discharged and, at the same time, the adsorbent is regenerated. However, moisture still slightly remaining accumulates in the adsorbent gradually and, thus, it is common to replace the adsorbent after a lapse of a certain period of time. Further, at the time of periodic inspection, it is confirmed that an oxygen-enriched gas is generated stably and, when an abnormality is occurring, replacement of the device itself is performed.

When the level of decrease in oxygen concentration exceeded a permissible range, an oxygen concentration abnormality alarm is activated, and the patient requests a vender to replace the oxygen concentrator. Until replacement of the device is completed, the patient has to breathe oxygen from an oxygen cylinder that is temporarily arranged at the patient's home, which impairs patient's quality of life considerably.

CITATION LIST

Patent Literature 1: Japanese Unexamined Patent Application No. 2002-253675
Patent Literature 2: Japanese Unexamined Patent Application No. 2000-516854
Patent Literature 3: Japanese Unexamined Patent Application No. 2013-13497
Patent Literature 4: WO 2014/046297

SUMMARY OF INVENTION

Technical Problem

Because many of users of an oxygen concentrator like this are patients with chronic respiratory diseases, such an oxygen concentrator is used for a long period of time. On the other hand, because a prescribed oxygen flow rate is determined according to severity of the disease, oxygen inhalation is carried out with prescription of only when doing work or for several hours a day in the case of a patient with mild symptoms. In the case of a patient who receives oxygen inhalation for 1 hour a day, for example, the time of use of the oxygen concentrator is 365 hours a year and the cumulative down time amounts to 8395 hours. When the oxygen concentrator is driven by such an intermittent operation, moisture penetrates into the adsorption cylinder during the down time of the device. Further, due to temperature change in the device caused by repetition of intermittent operation, dispersion of moisture inside the adsorption cylinder is accelerated. As a result, deterioration of the adsorbent proceeds rapidly, and sometimes causes decrease in the concentration of oxygen generated.

With regard to such an oxygen concentrator, in order to compensate for the decrease in oxygen concentration, there is known a technique, wherein the concentration of oxygen generated in a product gas is detected by an oxygen concentration sensor and, when the oxygen concentration decreased, compressor flow rate is increased to raise adsorption pressure, thereby compensating the oxygen concentration (Patent Literature 1). However, as the adsorbent deteriorates, optimum purge time gradually becomes short. Even if the compressor flow rate were increased with the purge time as it was set initially, there is not much effect on the recovery of concentration and, by raising the adsorption pressure, power saving characteristics are lost.

Furthermore, in the oxygen concentrator, there is also known a technique where in, when the concentration of oxygen in the product gas decreased as detected by an oxygen sensor, the oxygen concentration in the product gas is maintained by carrying out a feedback control based on the value of the oxygen concentration by changing a value of cycle time of adsorption and desorption, and the like (Patent Literatures 2 and 3). However, in these techniques, deterioration of the adsorbent is detected indirectly from the decrease in oxygen concentration and, therefore, it is difficult to determine an optimum cycle time of adsorption and desorption uniquely, and there is a problem that it takes time to adjust parameters such as each step time and the like to optimum states and to increase the oxygen concentration to a value suitable for treatment.

Furthermore, a technique set forth in Patent Literature 4 is based on a combination of control of the number of revolutions of a compressor and control of the purge time, wherein alteration of the purge time is made only after the number of revolutions of the compressor reached an upper limit value of the control. It is a problem that a considerable amount of time is required until the purge time alteration is actually performed, which has a large effect for increasing oxygen concentration against deterioration of the adsorbent.

Thus, the present invention provides a technique of detecting adsorption pressure, oxygen concentration, and environmental temperature of an oxygen concentrator during operation by respective sensors, judging a degree of deterioration of an adsorbent at regular intervals from the adsorption pressure and the oxygen concentration in a plurality of stages, and memorizing the data every time. Further, the present invention provides control to have the oxygen concentration recovered in a short period of time to a value suitable for treatment, by rapidly altering the purge time to an optimum value, when the degree of deterioration changes, the environmental temperature exceeds a threshold value, or the preset flow rate is changed, under the preset conditions in the table of an optimum purge time set in advance corresponding to each stage of deterioration, environmental temperature, and preset flow rate.

Solution to Problem

The present invention provides the following oxygen concentrator.

[1] A pressure swing adsorption-type oxygen concentrator comprising: a plurality of adsorption cylinders packed with an adsorbent which selectively adsorbs nitrogen rather than oxygen; a compressor which supplies compressed air to the adsorption cylinders; a flow path switching means for repeating at a prescribed timing, by sequentially switching flow paths between the compressor and each adsorption cylinder, an adsorption step wherein compressed air is supplied to each adsorption cylinder and an oxygen-enriched gas is taken out, a desorption step in which each adsorption cylinder is decompressed and the adsorbent is regenerated, and a purge step in which the oxygen-enriched gas from an adsorption cylinder at an adsorption step side is introduced to an adsorption cylinder at a desorption step side; a flow rate setting means which supplies the oxygen-enriched gas by adjusting the flow rate to a desired value; and a control means which controls operation of an oxygen concentration sensor to measure a concentration of the oxygen-enriched gas, a pressure sensor to detect a pressure of the adsorption cylinder, the compressor and the flow path switching means, wherein included are: a judgement means which controls the number of revolutions of the compressor based on a detected value of the oxygen concentration sensor and judges moisture-absorption deterioration of the adsorbent based on the detected value of the oxygen concentration sensor and a detected value of the pressure sensor; and a control means which, when criteria for judgment of moisture-absorption deterioration are satisfied, controls a switching time of the flow path switching means so that a time for the purge step is reduced shorter than a preset time, wherein the criteria for judgment of moisture-absorption deterioration are that the detected value of the oxygen concentration sensor is equal to or less than a reference concentration value which is a control value of the oxygen concentration in the oxygen-enriched gas and that the detected value of the pressure sensor is equal to or more than an adsorption pressure at which the oxygen concentration increases significantly before and after the control to reduce the purge time.

[2] The oxygen concentrator according to [1], wherein the judgement means includes a table of optimum purge times corresponding to the state of moisture-absorption deterioration of the adsorbent and judges the state of moisture-absorption deterioration of the adsorbent at specified time intervals during operation of the oxygen concentrator and, based on the judgement result, the control means performs alteration control of switching time of the flow path switching means.

[3] The oxygen concentrator according to [2], wherein the judgement means includes a reference pressure for judging the deterioration state of the adsorbent in a plurality of stages based on detected values of the pressure sensor and the oxygen concentration sensor during operation of the oxygen concentrator and also includes a memory means which memorizes judgement results of the stage of deterioration state set based on the reference pressure value.

[4] The oxygen concentrator according to any of [1] to [3], further including a temperature sensor which detects the temperature of the oxygen concentrator, wherein the judgement means includes a table of optimum purge times corresponding to detected values of the temperature sensor and preset flow rate values of the flow rate setting means and a control means which performs alteration of the purge time in preference to the flow rate control of the compressor when the temperature exceeds a threshold value or the preset flow rate is altered.

[5] The oxygen concentrator according to [4], wherein the judgement means includes criteria for judgment of deterioration state in a direction of improvement of the adsorbent and two conditions are satisfied that a detected value of the oxygen concentration sensor is equal to or more than a prescribed concentration value and that a peak value of the pressure sensor is equal to or less than a prescribed value.

[6] The oxygen concentrator according to [5], wherein the judgement means has a function of monitoring detected values of the oxygen concentration sensor before and after the purge time is altered when the criteria for judgement in the direction of improvement of the adsorbent are satisfied and judgement of the deterioration state is altered and, when the oxygen concentration is decreased after the alteration in purge time, of restoring the judgement of the deterioration state to an original state and, thereafter, not altering the judgement value even when the criteria for judgement in the direction of virgin material are satisfied.

[7] A method for judging deterioration of an adsorbent in a pressure swing adsorption-type oxygen concentrator equipped with adsorption cylinders packed with an adsorbent which selectively adsorbs nitrogen rather than oxygen, and generating oxygen by switching at a prescribed timing an adsorption step of supplying compressed air to each adsorption cylinder and taking out an oxygen-enriched gas, a desorption step of decompressing each adsorption cylinder and regenerating the adsorbent, and a purge step of introducing the oxygen-enriched gas from an adsorption cylinder at an adsorption step side to an adsorption cylinder at a desorption step side, comprising judging that the adsorbent is deteriorated when the concentration of the oxygen-enriched gas is equal to or less than the reference concentration value which is the control value of the oxygen concentration, and the pressure of the adsorption cylinder is equal to or more than the adsorption pressure at which the oxygen concentration increases significantly before and after control is performed to reduce the purge time.

Advantageous Effects of Invention

According to the oxygen concentrator of the present invention, it becomes possible not only to compensate for a decrease in the concentration of generated oxygen due to environmental changes of the device, but also to increase the concentration immediately to a value suitable for use even when the concentration of generated oxygen decreases due to deterioration of the adsorbent caused by intermittent operation, and further to design reduction of power consumption, long-term use of the oxygen concentrator, and lengthening of the maintenance interval.

Additionally, it becomes possible to detect the deterioration state of the adsorbent in an early stage, and there can be realized not only securement of quality as an oxygen concentrator but also optimization of an overhaul period and reduction of operating cost related to overhaul.

DESCRIPTION OF EMBODIMENTS

[Oxygen Concentrator]

An embodiment of an oxygen concentrator of the present invention will be described with reference to the drawings below.

Figure 1:
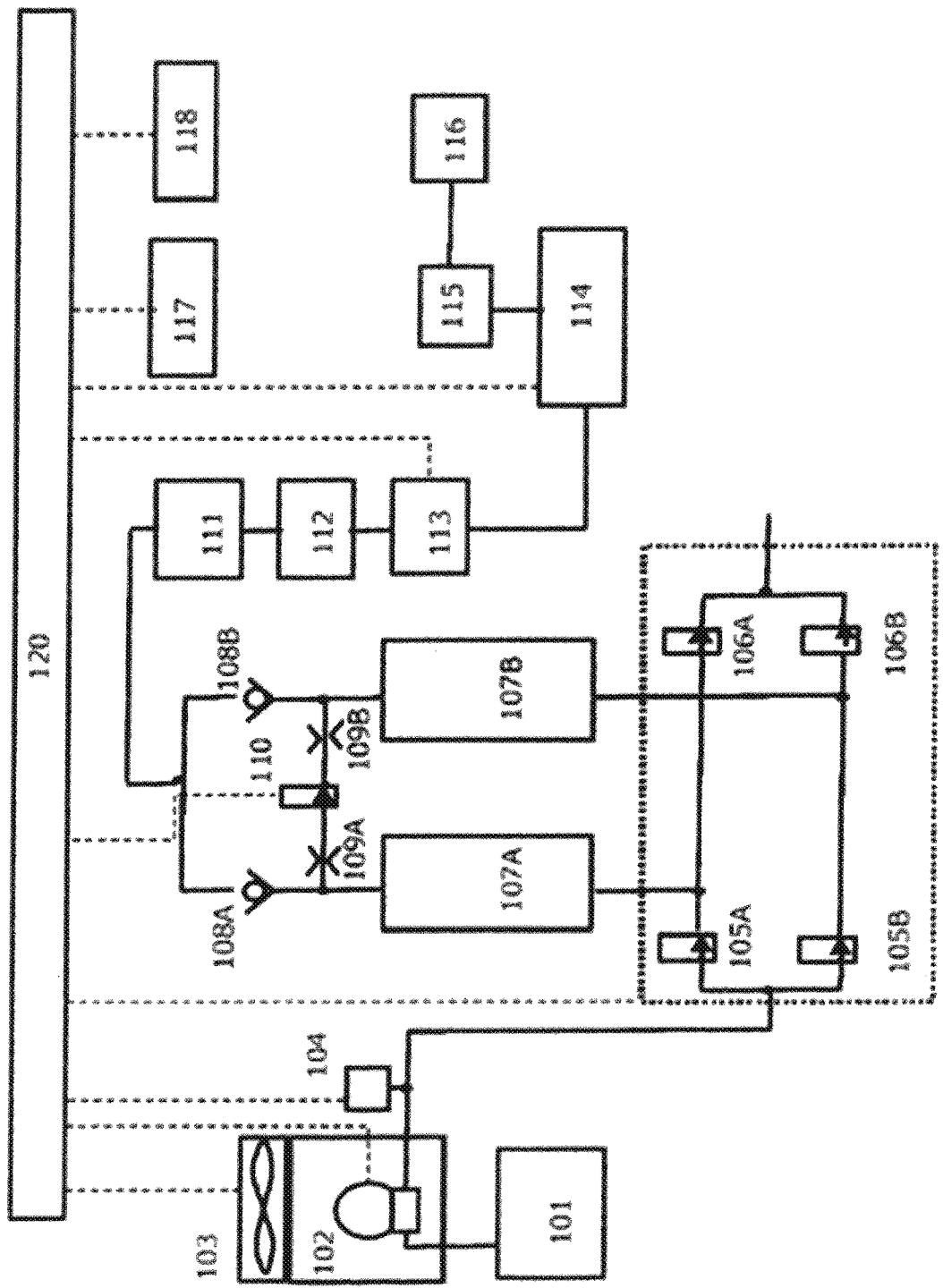
FIG. 1 is a schematic diagram showing a pressure swing adsorption-type oxygen concentrator according to an embodiment of the oxygen concentrator of the present invention.

FIG. 1 is a schematic constitutional diagram showing the pressure swing adsorption-type oxygen concentrator according to one embodiment of the present invention. The oxygen concentrator of the present invention comprises: a compressor 102 which supplies compressed air; two adsorption cylinders 107A and 107B packed with an adsorbent which selectively adsorbs nitrogen rather than oxygen; and supply valves 105A and 105B, exhaust valves 106A and 106B, and a pressure equalizing valve 110 which are flow path switching means that switch a sequence of an adsorption step, a desorption step, a pressure equalizing step, and the like. An oxygen-enriched gas generated by separation from the compressed air is adjusted to a prescribed flow rate by a control valve 113, freed from dust by a filter 115, and thereafter supplied to a user by using a nasal cannula 116.

The compressor 102 is the largest source of noise in the oxygen concentrator and also is a source of heat. By housing the same in a compressor box, reduction of noise is designed and temperature regulation is performed by means of a cooling fan 103.

Raw material air is brought into the oxygen concentrator from outside through an air intake port equipped with an external air intake filter 101 for eliminating foreign matter such as dust and the like. In this case, normal air contains about 21% oxygen gas, about 77% nitrogen gas, 0.8% argon gas, and 1.2% other gases such as carbon dioxide and the like. Such oxygen concentrator enriches an oxygen gas, which is essential for respiration, and extracts it.

To extract the oxygen-enriched gas, the raw material air compressed by the compressor 102 is supplied to an adsorption cylinder 107A and 107B packed with an adsorbent composed of zeolite, which selectively adsorbs nitrogen molecules rather than oxygen molecules, by opening and closing the supply valves 105A and 105B, and the exhaust valves 106A and 106B, while switching the flow path for adsorption cylinders sequentially, and by selectively removing nitrogen gas contained in the raw material air in the compressed adsorption cylinder at a concentration of about 77%. As such an adsorbent, there can be used molecular sieve zeolite such as Type 5A, Type 13X, Type Li-X, and the like.

The adsorption cylinder 107 is made of a cylindrical container packed with an adsorbent, and usually used are a one-cylinder type, a two-cylinder type and, in addition, a multi-cylinder type such as a three- or more-cylinder type. In order to produce the oxygen-enriched gas continuously and efficiently from the raw material air, it is desirable to use an adsorption cylinder of a two-cylinder type or a multi-cylinder type.

The compressor 102 may have merely a compressing function or both compressing and evacuating functions, and may be a two-head type swing air compressor as well as a rotational air compressor such as screw type, rotary type, scroll type and the like. Either alternating current or direct current may be used as a power source of an electric motor for driving the compressor.

In the adsorption step, compressed air supplied from the compressor 102 is fed to one adsorption cylinder 107A via the supply valve 105A. In the adsorption cylinder 107A in a compressed state, nitrogen in the air is adsorbed by the adsorbent, and the oxygen-enriched gas containing oxygen as a main component, which was not adsorbed, is taken out from a product exit side of the adsorption cylinder 107A and flows into a product tank 111 via check valve 108A which is installed to prevent the oxygen-enriched gas from flowing back into the adsorption cylinder.

On the other hand, the nitrogen gas adsorbed by the adsorbent packed in the adsorption cylinder needs to be desorbed from the adsorbent and purged, in order for the adsorbent to adsorb nitrogen again from newly introduced raw material air. For this purpose, in the desorption step, the other adsorption cylinder 107B is connected to an exhaust line via the exhaust valve 106B, and pressure in the adsorption cylinder 107B is switched from a compressed state to a state open to the air, thereby desorbing nitrogen adsorbed on the adsorbent in a compressed state and discharging the same into the air to regenerate the adsorbent. Furthermore, in this desorption step, an adsorption-purge step is performed in order to improve the efficiency of nitrogen desorption, wherein a part of the oxygen-enriched gas generated is taken out as a purging gas from the product exit side of the adsorption cylinder 107A during the adsorption step (adsorption-purge step) via orifices 109A and 109B, and the pressure equalizing valve 110, and flowed back from the product exit side of the adsorption cylinder 107B during the desorption step.

In the adsorption cylinder 107A, the adsorption step, the adsorption-purge step, the desorption step, and the desorption-purge step are performed sequentially and, in the adsorption cylinder 107B, the desorption step, the desorption-purge step, the adsorption step, and the adsorption-purge step are performed while being switched sequentially. Accordingly, the oxygen-enriched gas can be generated continuously.

The oxygen-enriched gas stored in the product tank 111 contains oxygen having a high concentration of, for example, 95%, and a necessary oxygen flow rate is set by a patient himself according to a doctor's prescription. A prescribed amount of the concentrated oxygen gas is supplied to the patient with pressure and a supply flow rate thereof controlled by means of a flow rate adjusting means such as a pressure regulating valve 112, a control valve 113, and the like. On the other hand, the flow rate and the oxygen concentration of the oxygen-enriched gas supplied to the patient are detected by an ultrasonic-type oxygen concentration/flow rate sensor 114 and, based on the detection results, the number of revolutions of the compressor 102, and an opening/closing times of the flow path switching means such as the supply valve 105, the exhaust valve 106, and the pressure equalizing valve 110 are controlled by an operating means such as CPU 120 and the like to control generation of oxygen.

The adsorption pressure is measured in terms of internal pressure of the adsorption cylinder or discharge pressure of the compressor, and is detected by a pressure sensor 104, as shown in FIG. 1, installed on a pipe at a discharge side of the compressor or a pressure sensor installed on the adsorption cylinder. The temperature in the oxygen concentrator is detected by a temperature sensor 117 disposed in the housing.

[Outline of Control]

Figure 2:
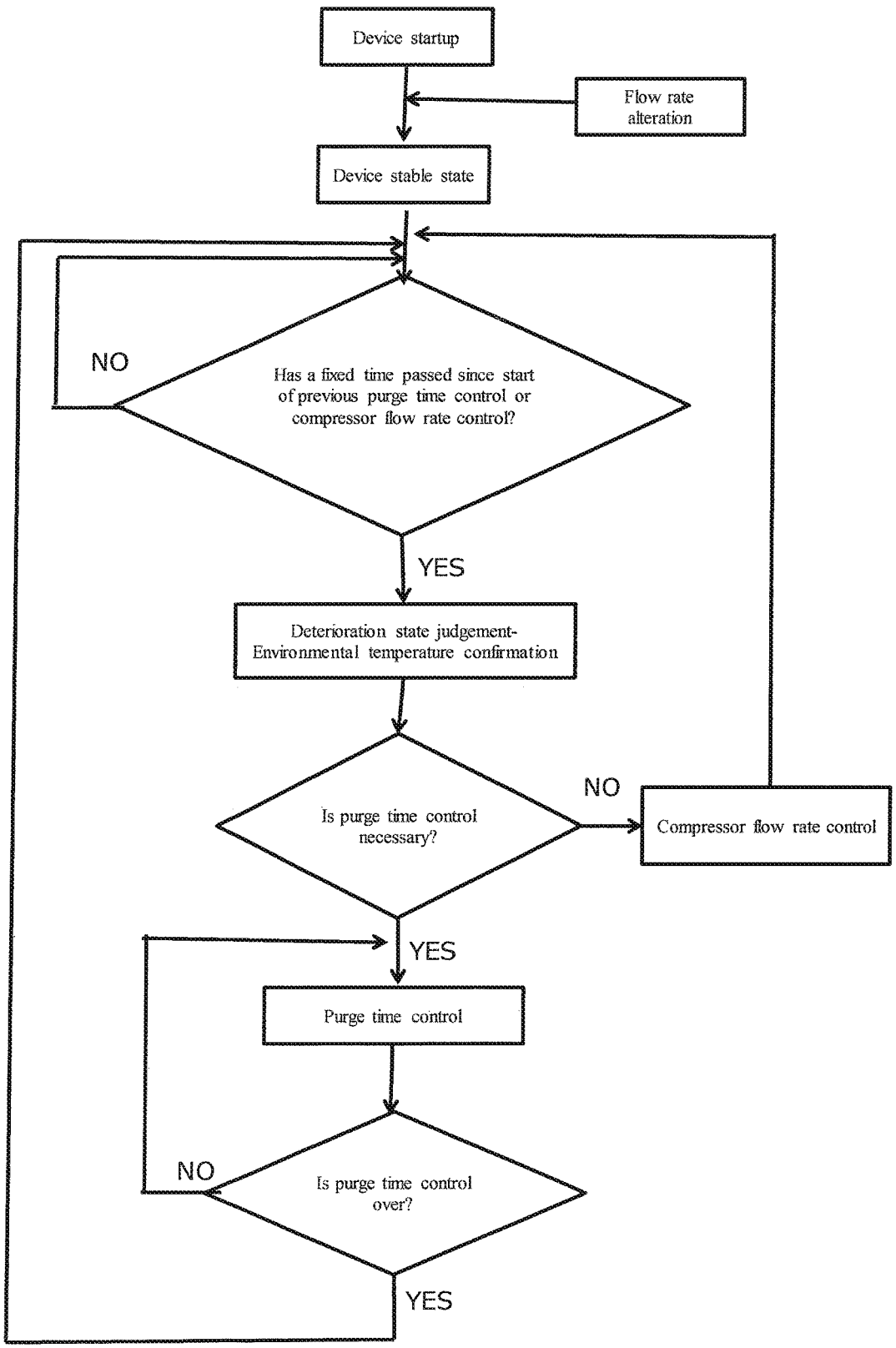
FIG. 2 shows a control flow chart of the oxygen concentrator of the present invention.

FIG. 2 is a diagram that illustrates the control operation flow of the oxygen concentrator of the present invention. The oxygen concentrator of the present invention, after it has reached a stable state after startup, performs confirmation and judgement of the deterioration state of the adsorbent as well as confirmation of the environmental temperature at preset regular intervals such as every 5 minutes or 10 minutes, namely at every control cycle, and judges whether purge time control, that is, alteration of the purge time is necessary or not.

When the purge time control is necessary, the flow is designed so that the purge time control is made to intervene in preference to the flow rate control of the compressor. However, when the alteration control of the purge time is unnecessary based on judgement of the deterioration state or confirmation of the environmental temperature, the compressor flow rate control shown in the flow diagram of FIG. 2 is carried out. The environmental temperature refers to the temperature of an environment in which the oxygen concentrator is being used, and it is not limited to the temperature of outside air and includes, depending on the position where the temperature sensor is disposed, the temperature inside the device, the temperature of intake air, the temperature of the adsorption bed, and the like.

The compressor flow rate control is a control whereby the oxygen concentration is maintained constant by controlling the number of revolutions of the compressor and controlling the adsorption pressure based on the detection results of the oxygen concentration. When the oxygen concentration fell below a predetermined threshold value due to moisture-absorption deterioration of the adsorbent and the like, control to increase the product oxygen concentration is performed by raising the adsorption pressure by increasing the number of revolutions of the compressor, thereby increasing the amount of air supplied to the adsorption cylinder. Further, when the oxygen concentration exceeded a predetermined threshold value, an energy saving control is performed, whereby the adsorption pressure is reduced by decreasing the number of revolutions of the compressor and the oxygen concentration is decreased to a predetermined concentration.

Judgement of the deterioration state and the environmental temperature is performed at every control cycle but, of the subsequent purge time control and compressor flow rate control, only one of them is performed. Priority of execution is in the order of the purge time control and the compressor flow rate control, and actual execution is as shown in FIG. 3.

Figure 3:
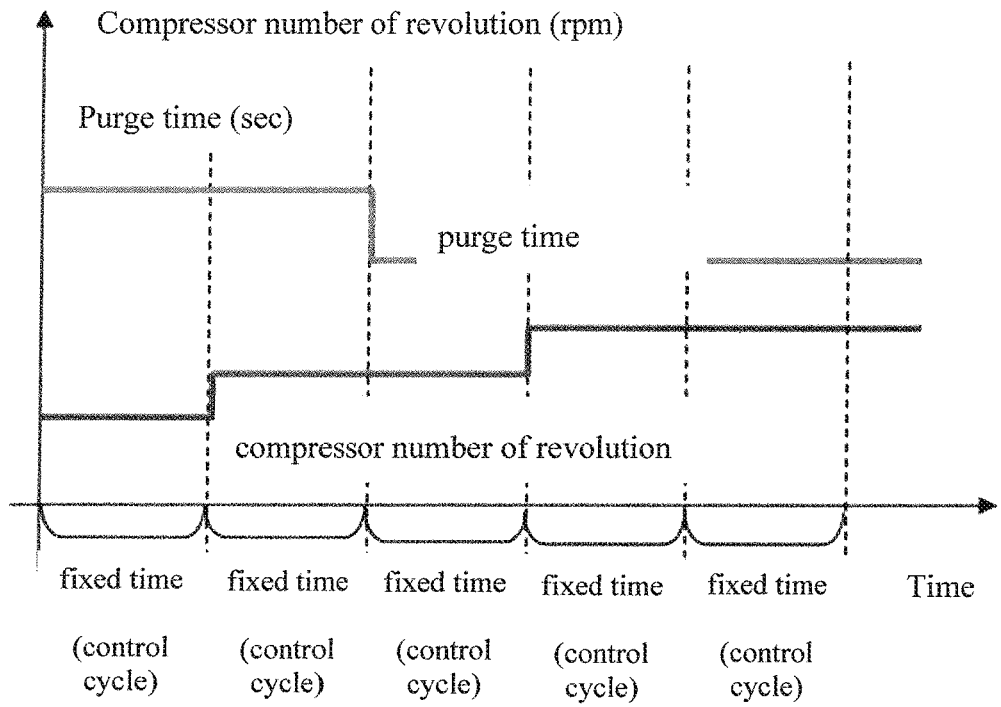
FIG. 3, FIG. 4, and FIG. 5 respectively show a relational diagram of purge time control and compressor flow rate control related to judgement of the deterioration state, a relational diagram showing transition of judgement of the deterioration state, and a relational diagram of the state of deterioration judgement, adsorption pressure, and environmental temperature.

FIG. 3 schematically shows a relationship between the compressor flow rate control and the purge time control. For example, when judgement of deterioration of the adsorbent is performed at a control cycle of 10 minutes and when a decrease of the oxygen concentration below the threshold value is observed but it does not satisfy the requirements for alteration of the purge time control, the compressor flow rate control is performed to maintain the oxygen concentration at the predetermined threshold value. At the next control timing, when the oxygen concentration fell below the predetermined threshold value and also the pressure reached or exceeded a threshold value and, in case the purge time control was judged to be necessary based on the judgement of the deterioration state, the compressor flow rate control is not performed but the purge time control is carried out preferentially. Such controls are performed repeatedly at every control cycle. In addition, in the last half of FIG. 3 is shown a case where the oxygen concentration fell below a range of control target value and a state in which further execution of the purge time control and the compressor flow rate control does not show an increase of the oxygen concentration and, thus, the control is unnecessary. When the preset flow rate is altered, the timer for control cycle is reset and, after the device reached a stable state, judgement of the deterioration state and confirmation of the environmental temperature are started again at every control cycle.

In addition, even though FIG. 3 is a schematic diagram where controls to alter the number of revolutions of the compressor and purge time are initiated at every control cycle but, in realty, the purge time alteration control is not initiated unless there is an alteration in the judgement of the deterioration state.

[Judgement of Deterioration State]

With regard to the judgement of the deterioration state, the state of deterioration of the adsorbent is judged in a plurality of stages from a peak pressure of the adsorption cylinder and the oxygen concentration in the product gas. Here, the deterioration state is described with three stages of virgin material, deterioration 1, and deterioration 2 as examples, but is not limited to these as long as the judgement is performed in two or more stages.

Figure 4:
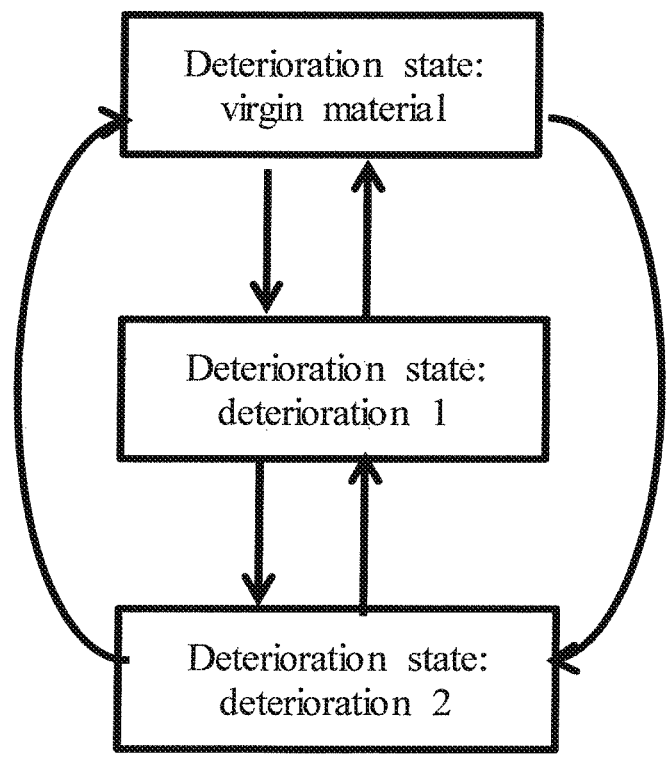

The deterioration state can shift, as shown in FIG. 4, to any deterioration state irrespective of the present deterioration state. For example, it is possible that the deterioration state can proceed rapidly as from virgin material to deterioration 2, skipping one stage, or that adsorption performance shifts in the direction of recovery as from deterioration 1 to virgin material.

The timing of the judgement is after startup of the oxygen concentrator or after alteration of the preset flow rate and, after the oxygen concentration in the product gas, adsorption pressure, and the like reached a stable state, the judgement is performed at every control cycle at regular time intervals. A deterioration judgement method is performed as follows.

As to a judgement in the direction of deterioration, the judgement is made when the following two conditions are satisfied: 1) the oxygen concentration is equal to or less than a certain value, and 2) the peak pressure of the adsorption cylinder is equal to or more than a deterioration-side pressure threshold value (virgin material_degr, deterioration-1_degr). For example, a judgement is made for virgin material→deterioration 1, deterioration 1→deterioration 2, or virgin material→deterioration 2. As to a judgement in the direction of virgin material, that is, in the direction of recovery of the adsorption performance, the judgement is made when the following two conditions are satisfied: 3) the oxygen concentration is equal to or more than a certain value, and 4) the peak pressure of the adsorption cylinder is less than a virgin material-side threshold value (deterioration 1_new, deterioration-2_new). For example, a judgement is made for deterioration 1→virgin material, deterioration 2→deterioration 1, or deterioration 2→virgin material.

Figure 5:
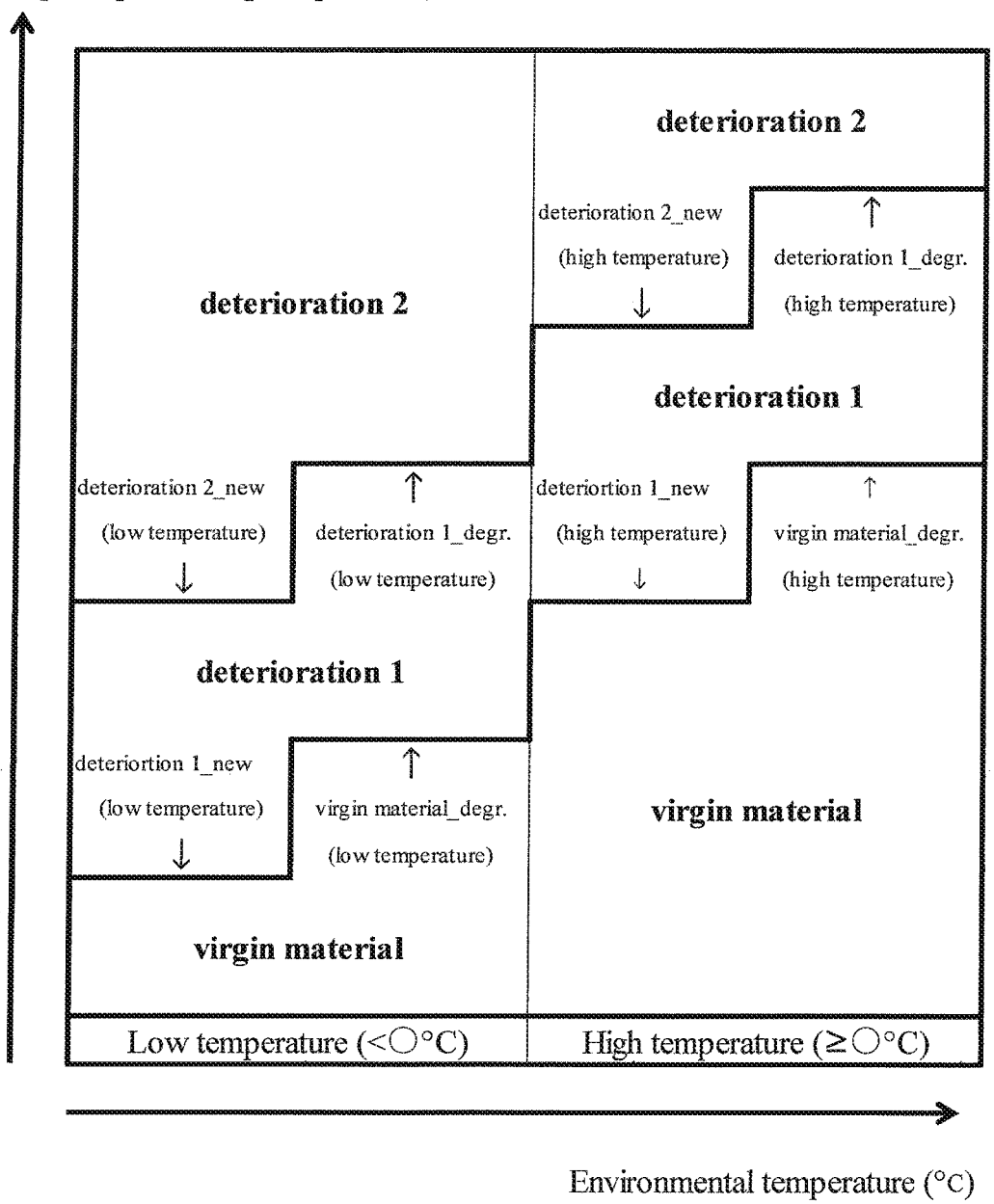

The set value of the oxygen concentration in the judgement in the direction of deterioration is set based on the lower limit of the oxygen-enriched gas to be supplied, for example, at 90% and the like. The set value in the judgement in the direction of virgin material is set at a value higher than the set value in the direction of deterioration. Each pressure threshold value is set for every preset flow rate. Further, as shown in FIG. 5, when an effect of temperature on the adsorption pressure is large such as when a range of the temperature used in the device is large, there may be set temperature threshold values such as on the high temperature side or on the low temperature side. And the pressure threshold values are set based on the preset flow rate and the temperature of intake air. Further, in order to prevent the judgement on the deterioration state from being altered frequently in the neighborhood of threshold values of pressure and temperature, hysteresis is provided for the pressure threshold value and the temperature threshold value.

In addition, the pressure of the adsorption cylinder in the present invention is not limited to the pressure in the adsorption cylinder but may be a pressure from which the adsorption pressure can be assumed, such as discharge pressure of the compressor, pressure of product tank in which product oxygen gas is stored, pressure in the pipes of the adsorption cylinder, and the like. Further, in addition to the pressure values, it is possible to judge the deterioration state of the adsorbent from the compressor flow rate and the oxygen concentration in the product gas, because the pressure in the adsorption cylinder can be calculated from a compressor flow rate value by installing a flow meter between the discharge side of the compressor and the adsorption cylinder.

[Setting of Pressure Threshold Value for Deterioration Judgement]

Figure 6:
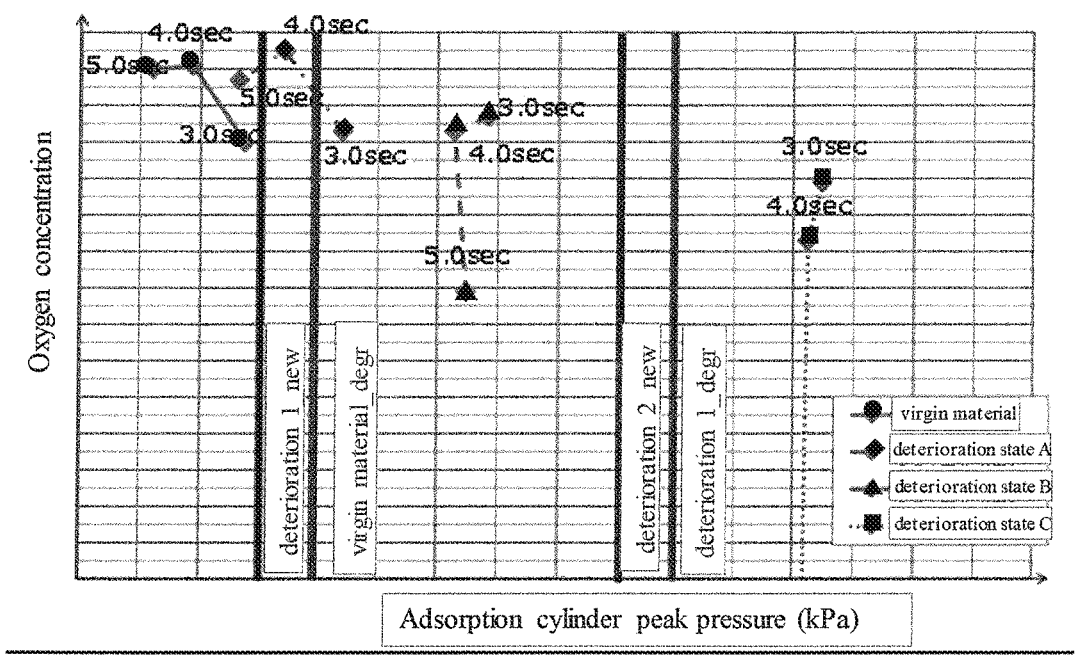
FIG. 6, FIG. 7, and FIG. 8 respectively show a diagram illustrating transition of pressure and optimum purge time accompanying progress of deterioration of the adsorbent, a relational diagram showing variation of oxygen concentration in an oxygen concentrator mounted with functions of deterioration state judgement, purge time changing operation, and compressor flow rate control of the present invention, and variation of oxygen concentration of an oxygen concentrator mounted only with the compressor flow rate control function.

FIG. 6 is a diagram which illustrates transition of pressure and optimum purge time with progress of deterioration of the adsorbent. Deterioration of the adsorbent proceeds in the order of virgin material→deterioration state A→deterioration state B→deterioration state C. As the deterioration state proceeds, the adsorption pressure increases gradually and an optimum point of the purge time gradually shifts to a shorter time. Furthermore, when the oxygen concentrator is operated under a state in which deterioration proceeded considerably at a purge time which is not optimum, it can be confirmed that the oxygen concentration decreases greatly.

The present invention utilizes the above characteristics and, in a situation in which the adsorption pressure has increased and the oxygen concentration is low, it is judged that the device is being operated in a state in which the adsorbent has deteriorated and the purge time is not optimum, judgement of the deterioration state is altered, for example, from virgin material to deterioration 1 or from deterioration 1 to deterioration 2, and the purge time is altered to a value in an optimum purge time table set beforehand based on respective deterioration states of the adsorbent.

The condition for the pressure threshold value (for example, virgin material_degr, deterioration 1_degr) when judging in the direction of deterioration is that, before and after reduction of the purge time, it is equal to or more than the adsorption pressure at which the oxygen concentration increases significantly.

In FIG. 6, when the pressure threshold value is at a pressure equal to or more than the pressure value of virgin material_degr, the oxygen concentration is significantly higher at a purge time of 4.0 seconds than a purge time of 5.0 seconds and, when the value is at a pressure value equal to or more than the pressure value of deterioration 1_degr, the concentration becomes significantly higher at a purge time of 3.0 seconds than the purge time of 4.0 seconds. In this case, the purge times of the virgin material, deterioration 1, and deterioration 2 will be set to 5.0 seconds, 4.0 seconds, and 3.0 seconds, respectively.

When the set value of the pressure threshold value in the direction of deterioration is set too low, the adsorbent will be judged to have deteriorated at an early stage and it follows, contrary to the expectation, that the oxygen concentration decreases. On the other hand, when the set value is set too high, the adsorbent will not be judged to have deteriorated and operation of the oxygen concentrator will be continued. Thus, it becomes impossible to increase the concentration effectively. It is desirable to set the pressure threshold value in a range of about ±10 kPa relative to the pressure value at which the oxygen value was judged to increase substantially before and after reduction of the purge time.

The state of the adsorbent sometimes shifts not in the direction of deterioration but in the direction of regeneration of the adsorbent and in the direction of virgin material, depending on the use environment and state alterations. Frequent switching of judgement values in the neighborhood of the threshold value can be prevented by setting the pressure threshold value when being judged in the direction of virgin material (deterioration 1_new, deterioration 2_new) to a value about 5 to 10 kPa lower relative to the pressure threshold value when being judged in the direction of deterioration (virgin material_degr, deterioration 1_degr). For example, there can be prevented frequent switching of the judgement values between, for example, virgin material_degr and deterioration 1_new and between deterioration 1_degr and deterioration 2_new.

Meanwhile, data in FIG. 6 were obtained under the condition of a constant flow rate from the compressor, and conditions are the same except the degree of deterioration of the adsorbent.

[Purge Time Control]

With a table ready, set beforehand from the preset flow rate, the deterioration judgement value, and the environmental temperature and, based on judgements at regular intervals according to the control cycle, control is performed to alter the purge time to a prescribed value when the deterioration judgement value is altered from the oxygen concentration and the value of adsorption pressure or, when the environmental temperature is altered. In addition, when the preset flow rate is altered, the control is performed once again from the beginning as shown in FIG. 2.

When the deterioration judgement shifted to a virgin material side and when the oxygen concentration decreased due to alteration in the purge time, that is, when the change in the oxygen concentration ($\Delta O_2$) before and after the alteration in the purge time became negative, the deterioration judgement value is returned to one before the alteration. When the adsorbent in a deteriorated state was erroneously judged to be in a virgin material state, it is assumed that the oxygen concentration decreases drastically due to the alteration in the purge time. Therefore, the oxygen concentrations before and after the alteration in purge time are compared and, when the concentration decreased, it is preferable to restore the deterioration judgement value to the original state and to restore the purge time to the original value. Further, when the original deterioration state is recovered once by the above operation, it is preferable thereafter, in order to prevent decrease in oxygen concentration due to erroneous judgement, to modify the design so that shifting in the direction of the virgin material side does not occur even when conditions for judging to shift in the direction of the virgin material side are satisfied.

When the purge time is altered, the alteration to a target purge time is not carried out all at once but the alteration is done over a plurality of times. Drastic alteration of a step time invites variation in the oxygen concentration, and it takes time for stabilization.

EXAMPLES

Figure 7:
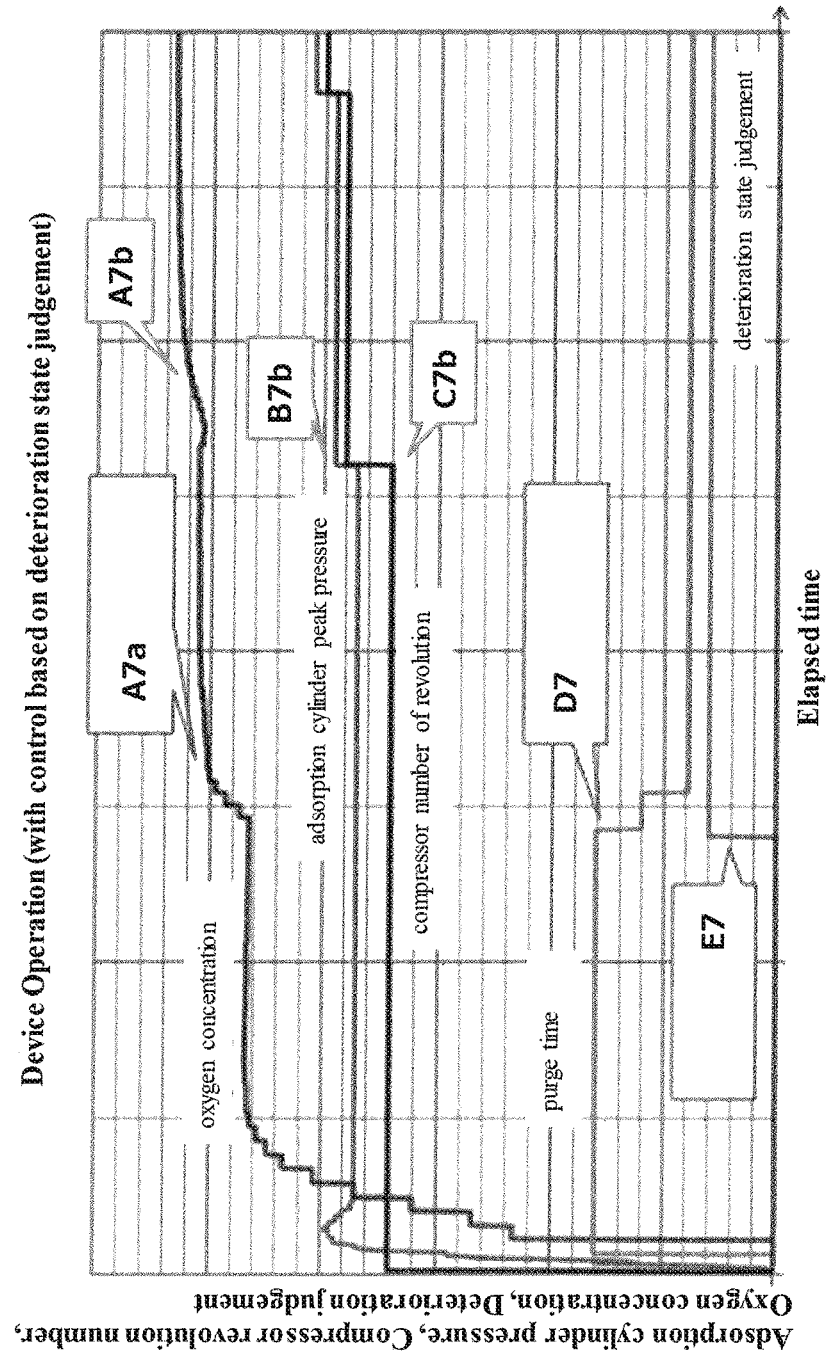
Figure 8:
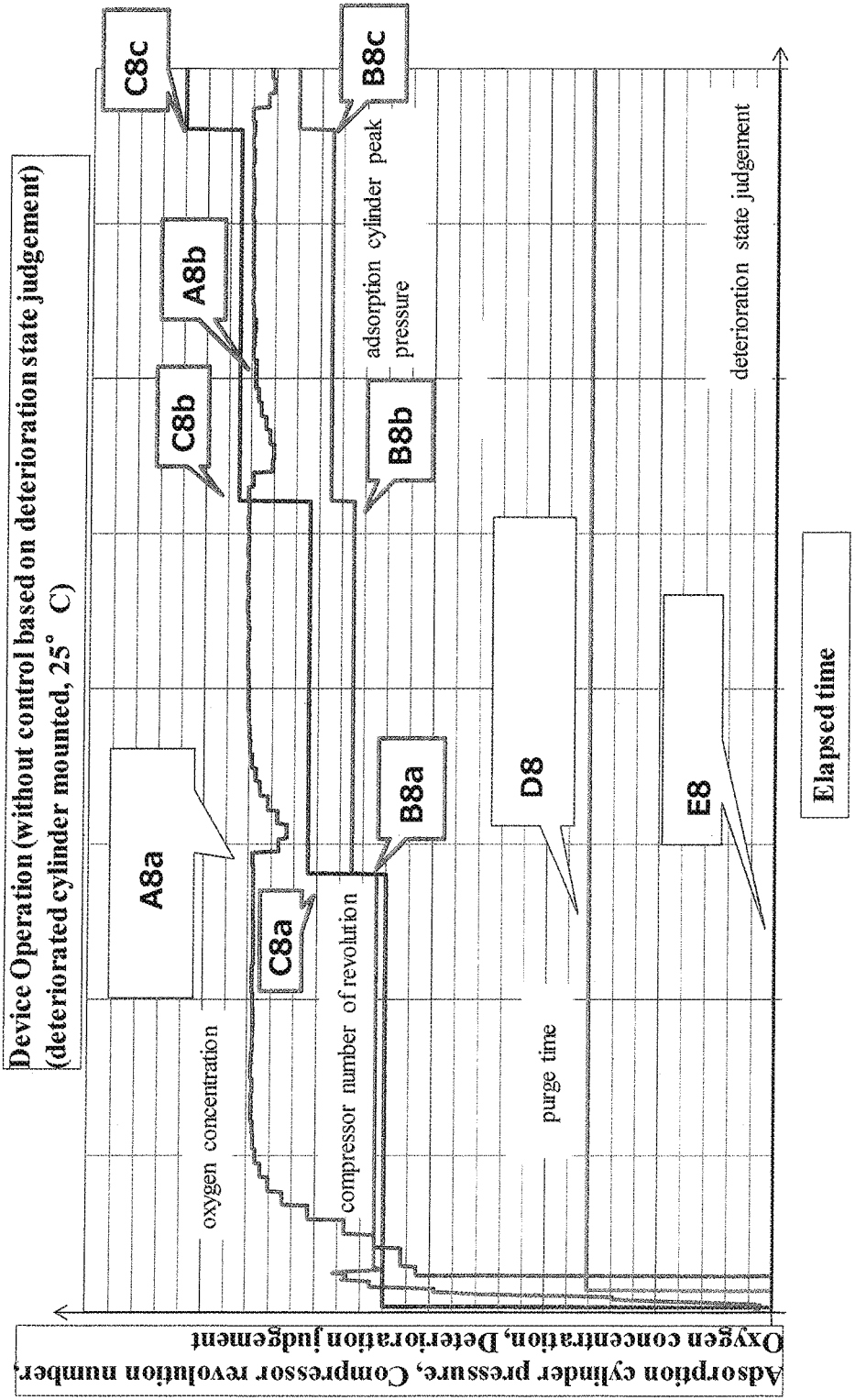

FIG. 7 illustrates the results of operation when a deteriorated adsorption cylinder was mounted on the oxygen concentrator of FIG. 1, which was mounted with the deterioration state judgement, and accompanying purge time alteration operation and the compressor flow rate control of the present invention. FIG. 8 similarly illustrates the results of operation when a deteriorated adsorption cylinder was mounted on the oxygen concentrator, which did not perform the deterioration state judgement and the purge time control but was mounted only with the compressor flow rate control.

Further, in both FIG. 7 and FIG. 8, the scales of time on the horizontal axis, concentration on the vertical axis, and the like are the same.

From FIG. 7, when the deterioration state judgement and the purge time alteration operation of the present invention are present, a deterioration judgement (E7) is performed after a fixed time from startup, at which the adsorbent is judged to have deteriorated from a virgin material state to deterioration 2 and, accordingly, an operation is performed to reduce the purge time from 5.0 seconds to 3.0 seconds in two stages (D7). By this operation, the oxygen concentration increases greatly (A7a). Also, compressor flow rate control which subsequently intervened (C7b) works effectively and an oxygen concentration increasing effect is observed (A7b) along with an increase in the adsorption cylinder peak pressure (B7b) and, as a result, an oxygen concentration suitable for treatment is reached in a short time after startup.

On the other hand, in the case in which deterioration state decision (E8) and purge time alteration operation (D8) are absent, shown in FIG. 8 as a comparison object, the number of revolutions of the compressor increases (C8a, C8b, and C8c) and the adsorption cylinder peak pressure also increases (B8a, B8b, and B8c) by the compressor flow rate control, but judgement of the deterioration state of the adsorbent is not performed and the device is not operated with a suitable purge time, such as by reducing the purge time. Therefore, there can be observed a situation in which, even when the adsorption pressure is increased, the oxygen concentration does not increase (A8a and A8b). It is clear that, under the condition in which the purge time is not appropriate, increase in the flow rate of the compressor is hard to contribute to the concentration. From these results, even when the oxygen concentration decreased due to deterioration of the adsorbent, the oxygen concentrator of the present invention can immediately increase the concentration to a value suitable for use. And there can be expected effects leading to reduction of power consumption, long-term use of the oxygen concentrator, and lengthening of the maintenance interval.

Such deterioration judgement of the adsorbent enables, when deterioration proceeded faster compared to an initially assumed overhaul time of the adsorbent, finding a replacement device early by looking at flags of the deterioration state judgement values and realizing optimization of the overhaul.

INDUSTRIAL APPLICABILITY

The oxygen concentrator of the present invention, as a medical oxygen concentrator, can be used as a source of oxygen supply for an oxygen inhalation therapy for patients suffering from respiratory organ diseases such as asthma, pulmonary emphysema, chronic bronchitis, and the like. More specifically, the present invention can provide an oxygen concentrator which can, even when the adsorbent deteriorated by moisture absorption due to intermittent operation and the like, maintain oxygen generated at a high concentration and can generate high concentration oxygen stably over a long period of time.

The invention claimed is:

1. A pressure swing adsorption-type oxygen concentrator comprising:
adsorption cylinders packed with an adsorbent which selectively adsorbs nitrogen rather than oxygen;
a compressor which supplies compressed air to the adsorption cylinders;

at least one flow path switching valve for repeating at a prescribed timing, by sequentially switching flow paths between the compressor and each adsorption cylinder, an adsorption step wherein the compressed air is supplied to each adsorption cylinder and an oxygen-enriched gas is taken out, a desorption step in which each adsorption cylinder is decompressed and the adsorbent is regenerated, and a purge step in which the oxygen-enriched gas from an adsorption cylinder at an adsorption step side is introduced to an adsorption cylinder at a desorption step side;

a flow rate setting means which supplies the oxygen-enriched gas by adjusting a flow rate to a desired value;

a controller which controls operation of an oxygen concentration sensor to measure an oxygen concentration of the oxygen-enriched gas, a pressure sensor to detect a pressure of the adsorption cylinder, the compressor and the at least one flow path switching valve; and a judgement means which controls a number of revolutions of the compressor based on a detected value of the oxygen concentration sensor and judges moisture-absorption deterioration of the adsorbent based on the detected value of the oxygen concentration sensor and a detected value of the pressure sensor, wherein the controller which, when criteria for judgment of moisture-absorption deterioration are satisfied, controls a switching time of the at least one flow path switching valve so that a time for the purge step is reduced shorter than a preset time, wherein the criteria for judgment of moisture-absorption deterioration are that the detected value of the oxygen concentration sensor is equal to or less than a reference concentration value which is a control value of the oxygen concentration in the oxygen-enriched gas and that the detected value of the pressure sensor is equal to or more than a pressure threshold value for deterioration judgement, and wherein the pressure threshold value for deterioration judgement is set in a range of about ±10 kPa relative to an adsorption pressure at which the oxygen concentration increases significantly before and after the control to reduce a purge time.

2. The pressure swing adsorption-type oxygen concentrator according to claim 1, wherein the judgement means includes a table of optimum purge times corresponding to the state of moisture-absorption deterioration of the adsorbent and judges the state of moisture-absorption deterioration of the adsorbent at specified time intervals during operation of the pressure swing adsorption-type oxygen concentrator and, based on a judgement result, the controller performs alteration control of the switching time of the at least one flow path switching valve.

3. The pressure swing adsorption-type oxygen concentrator according to claim 2, wherein the judgement means judges the deterioration state of the adsorbent in a plurality of stages based on detected values of the pressure sensor and the oxygen concentration sensor during operation of the pressure swing adsorption-type oxygen concentrator and also includes a memory which memorizes judgement results of the stage of deterioration state set.

4. The pressure swing adsorption-type oxygen concentrator according to claim 1, further including a temperature sensor which detects a temperature of the pressure swing adsorption-type oxygen concentrator, wherein the judgement means includes a table of optimum purge times corresponding to detected values of the temperature sensor and preset flow rate values of the flow rate setting means and the controller which performs alteration of the purge time in preference to a flow rate control of the compressor when the temperature exceeds a threshold value or the preset flow rate values is altered.

5. The pressure swing adsorption-type oxygen concentrator according to claim 4, wherein the judgement means includes criteria for judgment of deterioration state in a direction of improvement of the adsorbent and two conditions are satisfied that a detected value of the oxygen concentration sensor is equal to or more than a prescribed concentration value and that a peak value of the pressure sensor is equal to or less than a prescribed value.

6. The pressure swing adsorption-type oxygen concentrator according to claim 5, wherein the judgement means has a function of monitoring detected values of the oxygen concentration sensor before and after the purge time is altered when the criteria for judgement in the direction of improvement of the adsorbent are satisfied and judgement of the deterioration state is altered and, when the oxygen concentration is decreased after the alteration in the purge time, of restoring the judgement of the deterioration state to an original state and, thereafter, not altering the judgement value even when the criteria for judgement in the direction of virgin material are satisfied.

7. A method for judging deterioration of an adsorbent in a pressure swing adsorption-type oxygen concentrator equipped with adsorption cylinders packed with an adsorbent which selectively adsorbs nitrogen rather than oxygen, and generating oxygen by switching at a prescribed timing an adsorption step of supplying compressed air to each adsorption cylinder and taking out an oxygen-enriched gas, a desorption step of decompressing each adsorption cylinder and regenerating the adsorbent, and a purge step of introducing the oxygen-enriched gas from an adsorption cylinder at an adsorption step side to an adsorption cylinder at a desorption step side, comprising judging that the adsorbent is deteriorated when oxygen concentration of the oxygen-enriched gas is equal to or less than a reference concentration value which is a control value of the oxygen concentration, and a pressure of the adsorption cylinder is equal to or more than an adsorption pressure at which the oxygen concentration increases significantly before and after control is performed to reduce a purge time.

8. The pressure swing adsorption-type oxygen concentrator according to claim 1, wherein, when the detected value of the pressure sensor is more than the pressure threshold value for deterioration judgement, the pressure threshold value for deterioration judgement is set in a range of about ±10 kPa relative to a certain level of deterioration of the adsorbent is detected, a function to inform a user or a checker that the adsorbent is in a state in which replacement due to deterioration is necessary.

* * * * *